(12) United States Patent
Veneman et al.

(10) Patent No.: US 12,258,319 B2
(45) Date of Patent: Mar. 25, 2025

(54) PROCESS FOR MANUFACTURING A CYCLIC UREA ADDUCT OF AN ETHYLENEAMINE COMPOUND

(71) Applicant: NOURYON CHEMICALS INTERNATIONAL B.V., Arnhem (NL)

(72) Inventors: Rens Veneman, Amersfoort (NL); Antoon Jacob Berend Ten Kate, Arnhem (NL); Karl Fredrik Lake, Södertälje (SE); Jenny Valborg Therese Adrian Meredith, Årsta (SE); Michiel Jozef Thomas Raaijmakers, Deventer (NL); Slavisa Jovic, Utrecht (NL); Rolf Krister Edvinsson, Partille (SE); Hendrik Van Dam, Ede (NL); Eike Nicolas Kantzer, Uddevalla (SE); Ina Ehlers, Stenungsund (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 893 days.

(21) Appl. No.: 16/638,390

(22) PCT Filed: Aug. 7, 2018

(86) PCT No.: PCT/EP2018/071320
§ 371 (c)(1),
(2) Date: Feb. 11, 2020

(87) PCT Pub. No.: WO2019/030191
PCT Pub. Date: Feb. 14, 2019

(65) Prior Publication Data
US 2020/0199077 A1   Jun. 25, 2020

(30) Foreign Application Priority Data
Aug. 11, 2017  (EP) ..................... 17185947

(51) Int. Cl.
*C07D 233/32*   (2006.01)
*C07D 295/03*   (2006.01)

(52) U.S. Cl.
CPC ......... *C07D 233/32* (2013.01); *C07D 295/03* (2013.01)

(58) Field of Classification Search
CPC ............................. C07D 233/32; C07D 295/03
See application file for complete search history.

(56) References Cited

U.S. PATENT DOCUMENTS

| | | |
|---|---|---|
| 2,497,309 A | 2/1950 | Larson et al. |
| 2,868,801 A | 1/1959 | Steele |
| 4,387,249 A | 6/1983 | Harnden et al. |
| 4,503,250 A | 3/1985 | Herdle |
| 4,897,480 A | 1/1990 | Schoenleben |
| 11,292,768 B2 * | 4/2022 | Ten Kate ............... C07C 211/14 |
| 11,292,769 B2 * | 4/2022 | Lake .................... C07D 233/36 |

FOREIGN PATENT DOCUMENTS

| | | |
|---|---|---|
| CN | 101817764 A | 9/2010 |
| CN | 103539740 A | 1/2014 |
| CN | 104860886 A | 8/2015 |
| CN | 105860059 A | 8/2016 |
| EP | 496168 A1 | 7/1992 |
| GB | 622955 | 5/1949 |
| WO | 2017137531 A1 | 8/2017 |
| WO | 2017137532 A1 | 8/2017 |

OTHER PUBLICATIONS

Wu Chaoyong et al., Synthesis of urea derivatives from amines and CO2 in the absence of catalyst and solvent, Sep. 13, 2010, Issue: No. 12, Green Chemistry.
Lin Kong et al., Synthesis of Urea Derivatives from CO2 and Amines Catalyzed by Polythylene Glycol Supported Potassium Hydroxide without Dehydrating Agents, Mar. 23, 2010, Issue: No. 8, Synlett.
EPO, European Extended Search Report issued in European Application No. 17185947.3, dated Oct. 6, 2017.
EPO, International Search Report and Written Opinion issued in International Application No. PCT/EP2018/071320, dated Oct. 9, 2018.
Tomura, M., et al. "Highly efficient synthesis of cyclic ureas from CO2 and diamines by a pure CeO2 catalyst using a 2-propanol solvent", Green Chemistry, 2013, p. 1567-1577, vol. 15.
Kong, E., et al. "Synthesis of Urea Derivatives from CO2 and Amines Catalyzed by Polyethylene Glycol Supported Potassium Hydroxide without Dehydrating Agents," Synlett, 2010, p. 1276-1280.
Wu, C., et al., "Synthesis of urea derivatives from amines and CO2 in the absence of catalyst and solvent," Green Chemistry, 2010, p. 1811-1816, vol. 12, No. 10.

(Continued)

*Primary Examiner* — Sun Jae Yoo
(74) *Attorney, Agent, or Firm* — LKGLOBAL | Lorenz & Kopf, LLP

(57) ABSTRACT

A process is provided for manufacturing a cyclic urea adduct of an ethyleneamine compound, the ethyleneamine compound having a linear —NH—$CH_2$—$CH_2$—NH— group. The process includes, in an absorption step, contacting a liquid medium comprising an ethyleneamine compound having a linear —NH—$CH_2$—$CH_2$—NH— group with a $CO_2$-containing gas stream at a pressure of from about 1 to about 20 bara, resulting in the formation of a liquid medium into which $CO_2$ has been absorbed. The process further includes bringing the liquid medium to cyclic urea formation conditions, and, in an urea formation step, forming cyclic urea adduct of the ethyleneamine compound, urea formation conditions including a temperature of at least about 120° C., wherein the total pressure at the end of the urea formation step is at most about 20 bara, and wherein the temperature in the absorption step is lower than the temperature in the urea formation step.

20 Claims, No Drawings

(56) References Cited

OTHER PUBLICATIONS

Patent Office of the Cooperation Council, Examination Report issued in GC Application No. GC 2018-35781, dated Jan. 14, 2020.

* cited by examiner

PROCESS FOR MANUFACTURING A CYCLIC UREA ADDUCT OF AN ETHYLENEAMINE COMPOUND

CROSS-REFERENCE TO RELATED APPLICATION

This application is a U.S. National-Stage entry under 35 U.S.C. § 371 based on International Application No. PCT/EP2018/071320, filed Aug. 7, 2018, which was published under PCT Article 21(2) and which claims priority to European Application No. 17185947.3, filed Aug. 11, 2017, which are all hereby incorporated in their entirety by reference.

TECHNICAL FIELD

The present invention is directed to a process for manufacturing a cyclic urea adduct of an ethyleneamine compound by reacting an ethyleneamine compound with CO2.

BACKGROUND

Ethyleneamines consist of two or more nitrogen atoms linked by ethylene units. Ethyleneamines can be present in the form of linear chains H2N(—CH2-CH2-NH)p-H. For p=1, 2, 3, 4, . . . this gives, respectively, ethylenediamine (EDA), diethylenetriamine (DETA), linear triethylenetetramine (L-TETA), and linear tetraethylenepentamine (L-TEPA). It is clear that this range can be extended. With three or more ethylene units it is also possible to create branched ethyleneamines such as N(—CH2-CH2-NH2)3, trisaminoethylamine (TAEA). Two adjacent nitrogen atoms can be connected by two ethylene units to form a piperazine ring HN((—CH2-CH2-)2)NH. Piperazine rings can be present in longer chains to produce the corresponding cyclic ethyleneamines.

Hydroxyethylethyleneamines comprise at least one hydroxyl group connected to a nitrogen atom through an ethylene unit, wherein the nitrogen atom is connected via a further ethylene group to an amino-group. An example is aminoethylethanolamine or AEEA of the formula H2N—CH2-CH2-NH—CH2-CH2-OH. Chain-extended ethanolamines include monoethanolamine compounds of the formula H2N—(CH2-CH2-NH)q-CH2-CH2-OH, wherein q is 2 or higher.

Ethyleneamine compounds which contain a linear —NH—CH2-CH2-NH— moiety can be converted into urea derivatives thereof through reaction with CO2. These urea derivatives comprise a cyclic ethylene urea unit of the following formula.

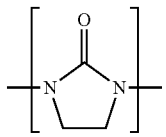

Ethyleneamine compounds comprising a cyclic ethylene urea unit can be used as starting material for chemical reactions, e.g., for the manufacture of chain-extended ethyleneamines or hydroxyethylethyleneamines. They may also be attractive products in themselves, e.g., for use in pesticides, pharmaceutical applications, and resins. In the present specification, Ethyleneamine compounds comprising one or more cyclic ethylene urea units are also indicated as urea derivatives or urea adducts.

It has been found that converting ethyleneamine compounds comprising at least one linear —HN—CH2-CH2-NH— moiety is not an easy process.

R. Nomura et al., Carbonylation of Amines by Carbon Dioxide in the Presence of an Organoantimony catalyst, J. Org. Chem. 1992, 57, 7339-7342, describes the formation of UAEEA from AEEA and CO2 using exotic catalysts such as triphenylstibine oxide in the presence of tetraphosphorus decasulphide.

U.S. Pat. No. 4,897,480 describes a process for manufacturing N,N'-dialkylsubstituted cyclic urea derivatives by reacting a diamine with carbon dioxide in the gas phase in the presence of an oxide of, e.g., aluminium, or in the presence of an aluminium silicate or magnesium silicate. The reaction is carried out in the gas phase by providing gaseous amine and CO2 and to a reactor containing the catalyst.

Chaoyong Wu et al., Synthesis of urea derivatives from amines and CO2 in the absence of catalyst and solvent, Green Chem., 2010, 12, 1811-1816, describes a process for manufacturing urea compounds, including cyclic ureas from amines by reaction with CO2. The reaction is carried out by first charging the reactor with amines, flushing it three times with CO2, and bringing it to reaction temperature. CO2 is then brought into the reactor with a high pressure liquid pump to the desired pressure. In table 2 process conditions are indicated as 180° C. and 10 MPa (100 bar).

De-Lin Kong et al., Synthesis of urea derivatives from CO2 and amines catalyzed by polyethylene glycol supported potassium hydroxide without dehydrating agents, Synlett 2010, No. 8, pp. 1276-1280, describes reaction of, among others, ethane-1,2-diamine and propane-1,2-diamine at 8 MPa (80 bar) CO2 pressure and 150° C. (423K) for 10 hours, in the presence of a catalyst. The minimum pressure is 2 MPa (20 bar). 8 MPa (80 bar) is concluded to be optimal.

Tamura et al., Highly efficient synthesis of cyclic ureas from CO2 and diamines by a pure CeO2 catalyst using a 2-propanol solvent, Green Chem., 2013, 15, 1567-1577, describes the reaction of ethylenediamine with CO2 in methanol over various catalysts, at a pressure of 0.5 MPa (5 bar) CO2 and a temperature of 160° C. (433K) for 1 hour. It is indicated that under these conditions the reaction does not proceed without a catalyst, and that for non-catalytic systems high CO2 pressure (above 5 MPa (50 bar)), and high temperature (above 150° C. (423 K) are required.

There is need in the art for a process for converting ethyleneamine compounds selected from the group of ethyleneamines and hydroxyethylethyleneamines and comprising at least one linear —NH—CH2-CH2-NH— moiety into their corresponding cyclic ethylene urea derivatives which process does not require the presence of metal-containing catalysts, while it can be performed under relatively mild conditions, in particular at low pressure, while obtaining good conversion. The present invention provides a process which meets this need.

BRIEF SUMMARY

In one embodiment, a process is provided for manufacturing a cyclic urea adduct of an ethyleneamine compound, the ethyleneamine compound having a linear —NH—CH2-CH2-NH— group. The exemplary process includes, in an absorption step, contacting a liquid medium comprising an ethyleneamine compound having a linear —NH—CH2-

CH2-NH— group with a CO2-containing gas stream at a pressure of 1-20 bara, resulting in the formation of a liquid medium into which CO2 has been absorbed. The process further includes bringing the liquid medium to cyclic urea formation conditions, and, in an urea formation step, forming cyclic urea adduct of the ethyleneamine compound, urea formation conditions including a temperature of at least about 120° C., wherein the total pressure at the end of the urea formation step is at most about 20 bara, wherein the temperature in the absorption step is lower than the temperature in the urea formation step.

It has been found that the process according to the embodiment makes it possible to obtain cyclic urea adducts in an efficient manner in the absence of metal-containing catalysts and to perform the process under relatively mild conditions, in particular relatively low pressure. More specifically, by separating the CO2 absorption step from the urea formation step, the CO2 absorption step can be carried out at relatively low temperatures and pressures. And because the CO2 is already present in the system at the beginning of the urea formation step, the pressure in the urea formation step does not need to be high. Further advantages of the present invention and specific embodiments thereof will become clear from the further specification.

In another embodiment, a process is provided for preparing ethyleneamines or urea derivatives thereof. The process includes manufacturing a cyclic urea adduct of an ethyleneamine compound, the ethyleneamine compound having a linear —NH—$CH_2$—$CH_2$—NH— group. The process further includes, in an absorption step contacting a liquid medium comprising an ethyleneamine compound having a linear —NH—$CH_2$—$CH_2$—NH— group with a $CO_2$-containing gas stream at a pressure of from about 1 to about 20 bara, resulting in the formation of a liquid medium into which $CO_2$ has been absorbed. Also, the process includes bringing the liquid medium to cyclic urea formation conditions, and in an urea formation step forming cyclic urea adduct of the ethyleneamine compound, urea formation conditions including a temperature of at least about 110° C., wherein the total pressure at the end of the urea formation step is at most about 20 bara, wherein the temperature in the absorption step is lower than that of the cyclic urea formation step. When the cyclic urea adduct of an ethyleneamine compound is a cyclic urea adduct of ethyleneamine, the process includes reacting the cyclic urea adduct of an ethyleneamine with an ethanolamine-functional compound, or a urea- or carbamate additive thereof. When the cyclic urea adduct of an ethyleneamine compound is a cyclic urea adduct of a hydroxyethylethyleneamine, the process includes reacting the cyclic urea adduct of a hydroxyethylethyleneamine with a ethyleneamine compound, or a urea- or carbamate additive thereof.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The invention will be discussed in more detail below.

In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

DETAILED DESCRIPTION

The ethyleneamine compound used as starting material in the present invention is an ethyleneamine compound selected from the group of ethyleneamines and hydroxyethylethyleneamines and comprising at least one linear —NH—CH2-CH2-NH— moiety.

The —NH—CH2-CH2-NH— moiety is linear, which means that it is not part of a piperazine ring. This is because —NH—CH2-CH2-NH— moieties in a piperazine ring cannot be converted to cyclic ethylene urea units of the following formula.

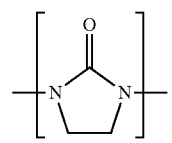

as this would require ring-opening.

Examples of ethyleneamines which are suitable for use in the present invention include linear ethyleneamine compounds having at least one —NH—CH2-CH2-NH— moiety. Compounds within this group are compounds of the formula H2N—(CH2-CH2-NH)p-H, wherein p is at least 1, in particular between 1 and 10. Examples of suitable compounds thus include ethylenediamine (EDA) wherein p is 1, diethylenetriamine (DETA) wherein p is 2, triethylenetetramine (L-TETA), wherein p is 3, and tetraethylenepentamine (L-TEPA), wherein p is 4.

The compounds may also include piperazine rings, where two nitrogen atoms are connected to each other via two ethylene groups. This does, however, not detract from the requirement that the compound should comprise at least one —NH—CH2-CH2-NH— moiety.

Examples of suitable piperazine-containing compounds are piperazinoethyl ethylenediamine (PEEDA),

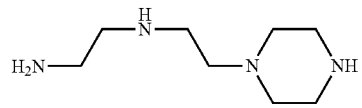

piperazinoethyl diethylenetriamine (PEDETA),

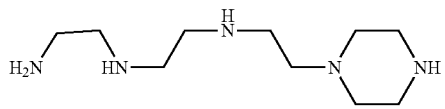

aminoethylpiperazinoethyl ethylenediamine (AEPEEDA)

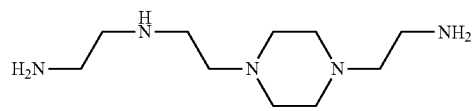 [SMILES: NCCNCCN1CCN(CCN)CC1]

The compounds may also include branched structures with tertiary amine bonds.

Examples of suitable branched compounds include aminoethyltriethylenetetramine (AETETA)

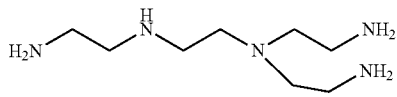 [SMILES: NCCNCCN(CCN)CCN]

Where the ethyleneamine compound is an ethyleneamine, ethylenediamine (EDA), diethylenetriamine (DETA), and triethylenetetramine (L-TETA) are preferred because they result in attractive urea derivatives.

Examples of hydroxyethylethyleneamines which are suitable for use in the present invention include linear hydroxyethylethyleneamine compounds having at least one —NH—CH2-CH2-NH— moiety. Compounds within this group are compounds of the formula HO—CH2-CH2-NH—(CH2-CH2-NH)q-H, wherein q is at least 1, in particular between 1 and 10. Examples of suitable compounds thus include aminoethylethanolamine (AEEA), where q is 1, and 2-[[2-[(2-aminoethyl)amino]ethyl]amino]-ethanol, also indicated as hydroxyethyldiethylenetriamine (HE-DETA), where q is 2. As for the ethyleneamines discussed above, the compounds may comprise piperazine entities or tertiary amine groups, as long as the compound still comprises at least one —NH—CH2-CH2-NH— moiety.

Where the ethyleneamine compound is a hydroxyethylethyleneamine, the use of aminoethylethanolamine (AEEA) and hydroxyethyl diethylenetriamine (HE-DETA) is considered preferred.

As will be discussed in more detail below, mixtures of ethyleneamines and hydroxyethylethyleneamines may also be used.

The first step of the process according to the invention is an absorption step, wherein a liquid medium comprising an ethyleneamine compound having a linear —NH—CH2-CH2-NH— group is contacted with a CO2-containing gas stream at a pressure of 1-20 bara resulting in the formation of a liquid medium into which CO2 has been absorbed.

The process according to the invention is intended to convert ethyleneamine compounds into cyclic ureas. Therefore, it is advantageous for the reaction medium to comprise substantial amounts of ethyleneamine compounds.

It may be preferred for the liquid medium used as starting material to comprise at least 30 wt. % of ethyleneamine compounds, in particular at least 50 wt. %. Depending on the further components in the system, it may be preferred for the liquid medium to comprise at least 70 wt. % of ethyleneamine compounds, or at least 80 wt. %, in some embodiments at least 90 wt. %.

Depending on its source, the liquid medium may comprise water. However, as water is not necessary for the reaction, and may, depending on the reaction conditions, promote hydrolysis of the cyclic urea adducts to be formed, it may be preferred to limit the amount of water in the liquid medium used as starting material. Therefore, in one embodiment, the liquid medium used as starting material comprises at most 50 wt. % of water, in particular at most 35 wt. % of water, still more in particular at most 20 wt. % of water. It may be preferred if the liquid medium used as starting material comprises less than 10 wt. % of water. In one embodiment, ethyleneamine compounds and water together make up at least 80 wt. % of the reaction medium, in particular at least 90 wt. %, more in particular at least 95 wt. %.

The liquid medium as described above is contacted with a CO2-containing gas stream. The CO2-containing gas stream can be a purified CO2-containing gas stream, containing, e.g., at least 95 vol. % of CO2. It is a particular advantage of the present invention that it is also possible to use gas streams containing lower, or even very low percentages of CO2. This makes it possible to use CO2-containing gas streams which are derived from industrial sources, or even to use air, optionally pre-treated. Therefore, in one embodiment of the present invention, the CO2-containing gas stream contains at most 70 vol. % of CO2, in particular at most 60 vol. % of CO2. The practical lower limit for the percentage of CO2 is 0.01 vol. %, as working below this limit will entail very large gas volumes. The CO2 content of the CO2-containing gas stream will depend on the available gas streams. For example, a suitable gas stream obtained from an industrial source may contain 4-60 vol. % of CO2.

In one embodiment the CO2-containing gas stream comprises 4-15 vol. % of CO2. An example of a suitable gas stream with a CO2 content in this range would be flue gas.

In another embodiment the CO2 containing gas stream comprises 20-40 vol. % of CO2. Examples of suitable gas streams with a CO2 content in this range are gas streams formed in the cement or steel industry, or in other industrial processes.

In addition to CO2, the CO2 containing gas stream can contain further gases and/or condensables such as water, hydrocarbons or amines. The main requirement for these gases and condensables is that their presence does not detrimentally affect the reaction. It is within the scope of the skilled person to determine the suitable further gases and condensables and the amount in which they can be present. Examples include nitrogen, noble gases, and water. It may be preferred to limit the amount of water in the gas stream, so as not to unnecessarily dilute the liquid medium. It is noted that the CO2 absorption at low temperature is quite selective. Therefore, if adequate purification is provided, the gas stream provided at low temperature can comprise less preferred compounds, as long as they are removed before the reaction mixture is brought to urea formation conditions.

Contacting the liquid medium with the CO2-containing gas steam in the absorption step will generally be carried out at a temperature between 0° C. and 200° C., taking into account that the temperature should be lower than the temperature in the urea formation step, as will be discussed below. A suitable temperature will also depend on the temperature of the CO2-containing gas stream.

The use of lower temperatures may be preferred, for reasons of energy efficiency. Therefore, in one embodiment, the temperature is at most 190° C., in particular at most 150° C. It may be preferred for the temperature to be at most 130° C., more in particular at most 110° C.

The minimum value is not critical to the present invention. However, higher values may result in better liquid-gas contact. Therefore, a value of at least 20° C., in particular at least 40° C. may be preferred.

The pressure during the absorption step will depend on the temperature and on the manner in which the CO2-containing gas stream is provided, and can be as low as anything as of 10 mbara, or more preferred it is at least 100 mbara. The pressure should be such that the medium comprising an ethyleneamine compound is in the liquid phase. On the other hand, it has been found that high pressures are not required in this step. Accordingly, the pressure. preferably is between 1 and 20 bara. It is more preferred, and possible in the present invention, to carry out the adoption step at much lower pressures, e.g., between 1 and 15 bara, even more in particular between 1 and 10 bara, yet even more in particular between 1 and 3 bara.

The pressure values given here are the total pressure. If the CO2 containing gas stream contains other gases in addition to CO2, the CO2 partial pressure will be lower.

The pressure in the system may vary, depending on the mode of operation. For example, if a large amount of CO2-containing gas is provided at the beginning of the absorption step (in batch operation), or intermittently during the process (fed-batch operation), the pressure will be highest just after the provision of the CO2-containing gas stream, and will decrease when the absorption of the CO2 in the reaction medium increases. The values for the pressure given above are the maximum pressure values.

The contacting of the liquid medium with the CO2-containing gas stream can be carried out in manners known in the art. In general, the CO2-containing gas stream will be contacted with the liquid medium by ensuring intimate contact between the two phases. As indicated above, the CO2-containing gas stream can be provided in batch fashion, or in fed-batch fashion. Of course, the CO2 may also be added in a continuous manner. This latter option has the advantage that the pressure can be kept relatively constant, which is advantageous for efficient operation. Suitable apparatus is known in the art. Examples include packed absorber columns, tray columns, and bubble columns. It may be attractive to provide additional means for agitating the reaction mixture to ensure good gas-liquid contact, that a homogeneous mixture is obtained and that the formation of high-viscosity spots and solid deposits is prevented, e.g., by providing stirring means.

The process of the invention comprises an absorption step and a urea formation step, also indicated as reaction step. In the absorption step CO2 is absorbed in the liquid reaction medium. In the reaction step the absorbed CO2 is reacted with the ethyleneamine compound to form an cyclic urea adduct. This means that in the urea formation step the provision of further CO2 is not required, and that the absorption step is carried out until sufficient CO2 has been absorbed in the liquid medium to achieve the desired conversion of ethyleneamine compound into cyclic ureas in the urea formation step.

Of course, some urea formation may also take place during the absorption step, especially at longer reaction times and higher temperatures. However, the majority of the urea formation will take place in the urea formation step where higher temperatures are employed. In particular, at least 50% of the total amount of urea formed in the process is formed in the urea formation step, more in particular at least 70%, still more in particular at least 80%, more in particular at least 90%. In this way, the temperature and pressure in the absorption step can be kept low.

As indicated above, the provision of further CO2 to the reaction medium during the urea formation step (in addition to the CO2 provided during the absorption step) is not required, and generally not attractive because it will increase the pressure during the urea formation step. If so desired for some reason, at most 20% of the total CO2 required to achieve the desired urea conversion is added during the urea formation step, in particular at most 10%.

In principle, one molecule of CO2 is required to convert one —NH—CH2-CH2-NH— moiety into a cyclic ethylene urea unit of the formula.

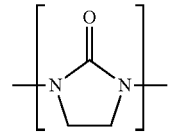

Depending on the degree of conversion desired, the absorption step can be carried out until at least 0.1 mole CO2 is absorbed per mole —NH—CH2-CH2-NH— moiety. It may be preferred to carry out the absorption step until at least 0.2 mole CO2 is absorbed per mole —NH—CH2-CH2-NH— moiety. Depending on the degree of conversion desired, the absorption step may be carried out until at least 0.5 mole CO2 is absorbed per mole —NH—CH2-CH2-NH— moiety. It may be preferred to carry out the absorption step until at least 0.7 mole CO2 is absorbed per mole —NH—CH2-CH2-NH— moiety, in particular at least 0.8 mole, more in particular at least 0.9 mole. Higher amounts are also possible, e.g., at least 1.0 mole. As the absorption of substantially more CO2 than the amount that can be converted into ethylene-urea moieties in embodiments is not preferred, the absorption step is generally carried out until at most 5 mole CO2 is absorbed per mole —NH—CH2-CH2-NH— moiety, in particular at most 3 mole, more in particular at most 2 mole.

Depending on the intended use of the reaction product it may be an attractive embodiment to produce a reaction mixture in which part of the —NH—CH2-CH2-NH— moieties have been converted into cyclic ethylene urea units, while part of the —NH—CH2-CH2-NH— moieties are not converted. Therefore, in one embodiment, the absorption step is carried out until from 0.1 to 0.95 mole CO2 is absorbed per mole —NH—CH2-CH2-NH— moiety, in particular between 0.2 and 0.8 mole/mole.

The amount of CO2 absorbed can be monitored, e.g., by monitoring the amount of CO2 in the gas stream after it has been contacted with the liquid medium.

How much of the CO2 that is provided to the system in the CO2-containing gas stream is absorbed in the liquid medium will depend, int. al., on the gas-liquid interaction in the absorption step, the amount of CO2 provided to the system, CO2 pressure, and reaction time.

The time required for the absorption step—which includes the total time for absorption steps if the absorption is done intermittently—is not critical for the present invention. It will depend on the gas-liquid interaction, and on the amount of CO2 provided to the liquid medium per unit of time. In general, the absorption step will take at least 15 minutes and at most 10 hours. It is preferred for the absorption step to be carried out in less than 8 hours, in particular less than 6 hours, more in particular less than 4 hours.

Once the absorption step has been completed, the liquid medium is brought to cyclic urea formation conditions. This generally means that the temperature of the liquid medium is increased to a value where cyclic urea moieties are formed. The minimum temperature for this step is 120° C. The exact temperature at which the cyclic urea moieties will be formed will depend on the nature of the ethyleneamine compounds to be converted. In general the compound in which the —NH—CH2-CH2-NH— moiety is connected to two hydrogen atoms is the easiest to convert, and thus requires the lowest temperature. This is ethylenediamine. Compounds where the —NH—CH2-CH2-NH— moiety is connected on one side to a hydrogen atom and on the other side to a further ethylene group are more difficult to convert, and require a higher temperature. Examples of these compounds are diethylenetriamine (DETA) and aminoethylethanolamine (AEEA), and the higher analogues of these compounds.

The temperature in the urea formation step is at least 120° C. At a temperature below 120° C., the reaction rate generally is too low to allow meaningful conversion within a reasonable time frame. It may be preferred for the reaction temperature to be at least 140° C., in particular at least 150° C., more in particular at least 170° C. The reaction is generally carried out at a temperature of at most 400° C. It may be preferred for the temperature to be at most 300° C., in particular at most 250° C., or even at most 220° C. Operating at a temperature of 170-220° C. is considered preferred.

The reaction time in the urea formation step is not critical, and will depend heavily on the temperature. In general, the reaction time will be at least 15 minutes, and at most 10 hours. By proper temperature selection it may be possible to carry out the reaction in a reaction time of at most 8 hours, in particular at most 6 hours, more in particular at most 4 hours.

In a preferred embodiment of the present invention, the cyclic urea formation step is carried out in a closed vessel. A closed vessel is a vessel in which no components are removed from or added to the reaction medium during the reaction. This will promote the formation of the cyclic urea adduct. The provision of further CO2 to the reaction medium in addition to the CO2 provided during the absorption step is not required, and generally not attractive because it will increase the pressure during the urea formation step. It has been found that it is particularly preferred to carry out the cyclic urea formation step in a vessel with the volume of the liquid medium in the vessel making up at least 50% of the total volume of the vessel (including head space), in particular at least 70%, more in particular at least 85%. This has also been found to increase the formation of cyclic urea adducts.

In the process according to the invention the pressure at the end of the urea formation step is at most 20 bara at reaction temperature. It is a feature of the present invention that the pressure in the urea formation step can be relatively low. Depending on the pressure in the absorption step, the pressure at the end of the cyclic urea formation step may be below 15 bara, in particular below 10 bara, in some embodiments below 5 bara, or even below 3 bara. Subatmospheric operation is not attractive. Therefore, the minimum pressure will be about 1 bara. The pressure may change during the urea formation step. The pressure values given here are the pressure values at the end of the urea formation step at reaction temperature.

In one embodiment the pressure at the end of the urea formation step is lower than the pressure at the end of the absorption step.

It will be evident to the skilled person that preferred embodiments as described above can be combined as long as they are not mutually exclusive.

A particularly preferred embodiment of the process according to the invention is a process for manufacturing a cyclic urea adduct of an ethyleneamine compound, the ethyleneamine compound having a linear —NH—CH2-CH2-NH— group, the process comprising the steps of in an absorption step contacting a liquid medium comprising an ethyleneamine compound having a linear —NH—CH2-CH2-NH— group with a CO2-containing gas stream at a pressure 1 1-10 bara, in particular 1-5 bara, more in particular 1-3 bara, at a temperature of 20-110° C., in particular 50-110° C., wherein the CO2-containing gas stream is added in a continuous manner or in a fed-batch manner, in particular in a continuous manner, resulting in the formation of a liquid medium into which CO2 has been absorbed, bringing the liquid medium to cyclic urea formation conditions at a temperature of 170-220° C. and a pressure of 1-10 bara, in particular 1-5 bara, more in particular 1-3 bara, in a closed vessel, resulting in the formation of cyclic ethylene ureas.

In one embodiment an intermediate purification step can be carried out between the absorption step and the urea formation step to remove undesirable compounds introduced with the CO2-containing gas stream. However, if the CO2-containing gas stream comprises undesirable compounds it may also be attractive to remove them from the CO2-containing gas stream before providing it to the absorption step.

The process according to the invention can be carried out in the absence of a metal-containing catalyst. Within the context of the present specification a catalyst is intended to refer to a component which is capable of increasing the rate of reaction in which the ethyleneamine compound is converted into its corresponding urea derivative.

The reaction generates the urea derivatives of the ethyleneamine compounds. During the reaction, the —NH—CH2-CH2-NH— group in the ethyleneamine starting compound is converted to a cyclic ethylene urea unit of the formula

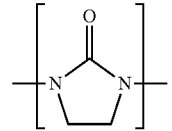

For example, ethylenediamine (EDA) is converted to the urea derivative ethyleneurea (EU), diethylenetriamine (DETA) is converted to the urea derivative UDETA, triethylenetetramine (L-TETA) is converted to one or more urea derivatives UTETAs, tetraethylenepentamine (L-TEPA) is converted to one or more urea derivatives UTEPAs, aminoethylethanolamine (AEEA) is converted to the urea derivative UAEEA, and hydroxyethyldiethylenetriamine (HE-DETA) is converted to its urea derivative HE-UDETA.

Piperazinoethylethylenediamine (PEEDA) is converted to its urea derivative UPEEDA. As will be evident to the skilled person, compounds with two distinct —NH—CH2-CH2-NH— groups can form di-urea additives. An example is the di-urea additive of triethylenetetramine (DUTETA). Some of the cited compounds are illustrated below:

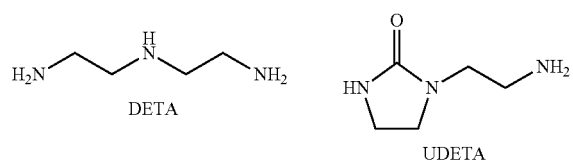

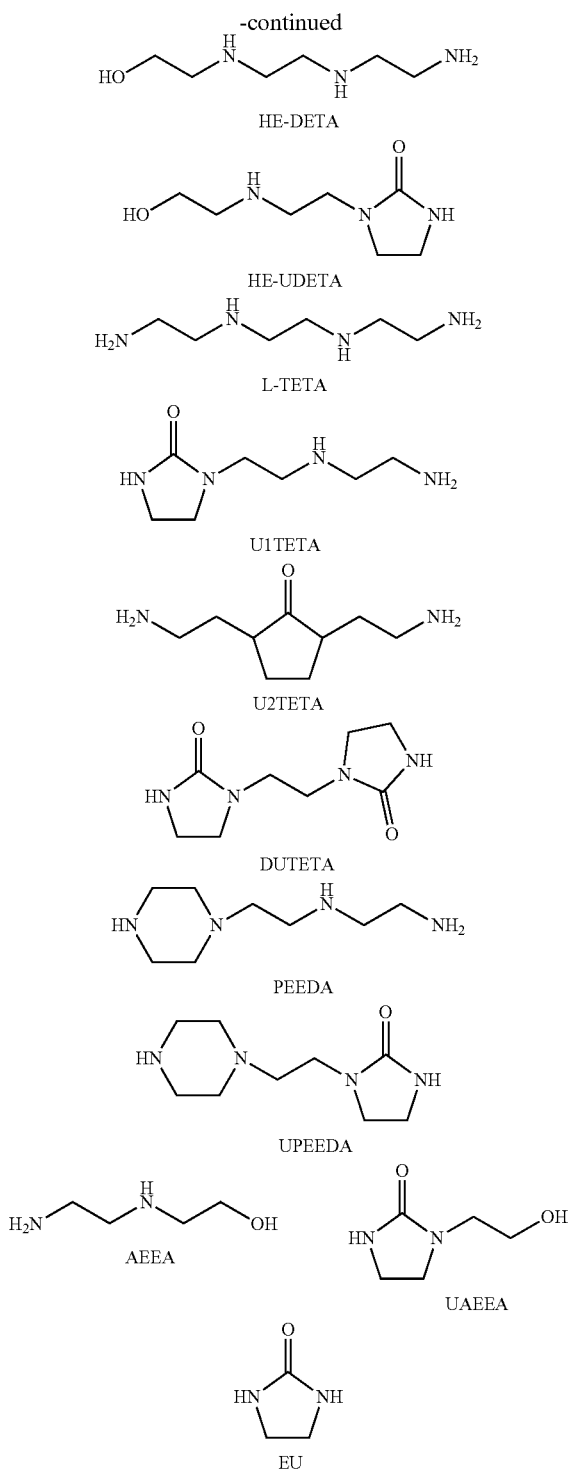

It has been found that the reaction rate of the process according to the invention can be increased if the liquid reaction medium comprises ethylenediamine (EDA) or monoethanolamine (MEA). Ethylenediamine comprises a linear —NH—CH2-CH2-NH— group and can thus be used as single compound in the reaction medium to form cyclic ethylene ureas. It can also be combined with other compounds which may or may not comprise a linear —NH—CH2-CH2-NH— group. Monoethanolamine does not comprise a linear —NH—CH2-CH2-NH— group and will thus be combined in the liquid medium with a compound which comprises a linear —NH—CH2-CH2-NH— group and can thus form a cyclic urea.

It has been found that the present invention is particularly suitable for the manufacture of a starting composition for manufacturing higher ethyleneamines or urea derivatives thereof.

For example, U.S. Pat. No. 4,503,250 describes a process for the manufacture of predominantly linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase. The derivative of carbonic acid may be a urea compound.

Previously filed non-prepublished international application EP2017/052946, now published as WO2017/137531, describes a process to prepare ethyleneamines of the formula NH2-(CH2-CH2-NH-)pH wherein p is at least 3 or derivatives thereof wherein one or more units —NH—CH2-CH2-NH— may be present as a cyclic ethylene urea unit or between two units —NH—CH2-CH2-NH— a carbonyl moiety is present, by reacting an ethanolamine-functional compound, an amine-functional compound in the presence of a carbon oxide delivering agent, wherein the molar ratio of carbon oxide delivering agent to amine-functional compound is at least 0.6 to 1.

Previously filed non-prepublished international application EP2017/052948, now published as WO2017/137532, describes a process to prepare ethyleneamines of the formula NH2-(CH2-CH2-NH-)pH wherein p is at least 3 or derivatives thereof wherein one or more units —NH—CH2-CH2-NH— may be present as a cyclic ethylene urea unit or between two units —NH—CH2-CH2-NH— a carbonyl moiety is present, by reacting an ethanolamine-functional compound, an amine-functional compound in the presence of a carbon oxide delivering agent, wherein the molar ratio of ethanolamine-functional compound to amine-functional compound is at least 0.7:1 and the molar ratio of carbon oxide delivering agent to amine-functional compound is at least 0.05:1.

Previously filed non-prepublished international application EP2017/052945, now published as WO/2017/137530, describes a process to prepare ethyleneamines of the formula NH2-(CH2-CH2-NH-)pH wherein p is at least 2 wherein one or more units —NH—CH2-CH2-NH— are present as a piperazine unit or precursors thereof wherein optionally one or more units —NH—CH2-CH2-NH— are present as a cyclic ethylene urea unit or between two units —NH—CH2-CH2-NH— a carbonyl moiety is present, by reacting an ethanolamine-functional compound, an amine-functional compound in the presence of a carbon oxide delivering agent, wherein at least one of the amine-functional compound or the ethanolamine-functional compound contains a piperazine unit, and the reaction is performed in a liquid that comprises water.

In all applications it is indicated that the ethanolamine-functional compound and the carbon oxide delivering agent can be added in the form of a single compound. The amine-functional compound and the carbon oxide delivering agent can also be added in the form of a single compound. The present invention makes it possible to prepare starting compounds which are urea derivatives of amine-functional compounds or of ethanolamine compounds, which are suitable for use as starting material in the manufacture of higher ethyleneamines or urea derivatives thereof.

Therefore, in one embodiment, the invention pertains to a process for preparing ethyleneamines or urea derivatives thereof, which process comprises the steps of
- a) manufacturing a cyclic urea adduct of an ethyleneamine compound, the ethyleneamine compound having a linear —NH—CH2-CH2-NH— group, the process comprising the steps of
  - in an absorption step contacting a liquid medium comprising an ethyleneamine compound having a linear —NH—CH2-CH2-NH— group with a CO2-containing gas stream at a pressure of 1-20 bara, resulting in the formation of a liquid medium into which CO2 has been absorbed,
  - bringing the liquid medium to cyclic urea formation conditions, and in an urea formation step forming cyclic urea adduct of the ethyleneamine compound, urea formation conditions including a temperature of at least 110° C., wherein the total pressure at the end of the urea formation step is at most 20 bara, wherein the temperature in the absorption step is lower than that of the cyclic urea formation step,
- b1) where the cyclic urea adduct of an ethyleneamine compound is a cyclic urea adduct of ethyleneamine, reacting the cyclic urea adduct of an ethyleneamine with an ethanolamine-functional compound, or a urea- or carbamate additive thereof, or
- b2) where the cyclic urea adduct of an ethyleneamine compound is a cyclic urea adduct of a hydroxyethylethyleneamine, reacting the cyclic urea adduct of a hydroxyethylethyleneamine with a ethyleneamine compound, or a urea- or carbamate additive thereof.

The manufacture of ethyleneamines by the process described above is in essence the reaction between an ethyleneamine compound and an ethanol amine compound wherein either compound can be at least partially in the form of a urea derivative, wherein the urea derivative is prepared by the process described above. The description of the process as provided above will thus also apply to step a) of the process of the preceding paragraph.

Step b (whether b1 or b2) is preferably performed at a temperature of at least 100° C. The temperature should preferably be lower than 400° C. More preferably the temperature is between 200 and 360° C. Even more preferably the temperature is between 230 and 350° C. Most preferably the temperature is between 250 and 320° C. In embodiments where the ethanolamine-functional compound is monoethanolamine the most preferred temperature range is between 230 and 290° C.

In step b the reaction time is in an embodiment between 5 minutes and 15 hours, preferably between 0.5 and 10 hours, more preferably between 1 and 6 hours.

The reaction product of step b) will comprise one or more compounds in the form of urea adducts. In one embodiment, the product is subjected to a CO removal reaction to convert the urea adduct into amine compounds. Within the context of the present specification, a CO removal reaction is intended to refer to any reaction wherein the urea adduct is converted into the corresponding amine compound by removal of the carbonyl group and addition of two hydrogen atoms.

In one embodiment of the present invention the liquid medium comprising an ethyleneamine compound having a linear —NH—CH2-CH2-NH— group will comprise both an ethyleneamine compound and an ethanolamine compound. In this case, the reaction product from step a) can be directly reacted further. The ethyleneamine compound used in this process has a linear —NH—CH2-CH2-NH— group and can therefore be converted to a cyclic urea adduct. The ethanolamine compound may have a linear —NH—CH2-CH2-NH— group, e.g., in the case of aminoethylethanolamine (AEEA) of the formula H2N—CH2-CH2-NH—CH2-CH2-OH. However, it is also possible for the ethanolamine compound to be monoethanolamine (MEA). This compound will not be converted to a cyclic urea adduct. Not wishing to be bound by theory, it is believed that this compound will be converted to a carbamate of the following formula:

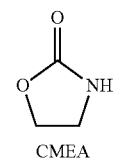

CMEA

In this case it may be preferred if the liquid medium used a starting material comprises at least 30 wt. % of the total of ethyleneamine compounds and monoethanolamine, in particular at least 50 wt. %. Depending on the further components in the system, it may be preferred for the liquid medium to comprise at least 70 wt. % of the total of ethyleneamine compounds and monoethanolamine, or at least 80 wt. %, in some embodiments at least 90 wt. %.

Therefore, the invention also pertains to a process preparing ethyleneamines or urea derivatives thereof, which process comprises the steps of
- a) in an absorption step contacting a liquid medium comprising an ethyleneamine having a linear —NH—CH2-CH2-NH— group and an ethanolamine with a CO2-containing gas stream at a pressure of 1-20 bara, resulting in the formation of a liquid medium into which CO2 has been absorbed,
  - bringing the liquid medium to cyclic urea formation conditions, and in an urea formation step forming cyclic urea adduct of the ethyleneamine and cyclic urea adduct or carbamate adduct of ethanolamine, with urea formation conditions including a temperature of at least 110° C., wherein the total pressure at the end of the urea formation step is at most 20 bara, wherein the temperature in the absorption step is lower than that in the urea formation step, and
- b) reacting the cyclic urea adduct of the ethyleneamine with the ethanolamine or the urea or carbamate derivative thereof.

In this case, the molar ratio between the ethyleneamine having a linear —NH—CH2-CH2-NH— group and the ethanolamine generally is between 0.1:1 and 10:1, more in particular between 0.5:1 and 5:1.

As will be evident to the skilled person, preferred embodiments of various aspects of the present invention can be combined, unless they are mutually exclusive.

In the present specification, mention is made of urea adducts and urea derivatives. These terms are used interchangeably to refer to compounds wherein two nitrogen atoms are connected through a —C(O)— moiety. The terms CO adducts and CO2 adducts are also used interchangeably. They refer to compounds wherein either two nitrogen atoms are connected through a —C(O)— moiety or a nitrogen atom and an oxygen atom are connected through a —C(O)— moiety.

The present invention will be elucidated by the following examples, without being limited thereto or thereby.

EXAMPLE 1

Conversion of EDA and AEEA into their Cyclic Urea Adducts Using CO2 at Different Pressure Levels To investigate the effect of CO2 pressure on the conversion of aminoethylethanolamine (AEEA) and ethylenediamine (EDA) into their cyclic urea adducts, four experiments were carried out.

Mixtures of EDA and AEEA were combined with CO2 in a two-step process. In the first step, the CO2 was loaded into the amine mixture at temperatures above 50° C. In the second step of the process, the loaded mixture was heated to temperatures above 150° C. for two hours in a closed reactor vessel to obtain a mixture of amines and their cyclic urea adducts. The pressure at the end of the second step (at reaction temperature) was below 15 bara for all experiments. After two hours of reaction time, the reaction mixture was cooled down and analyzed using GC-FID, which stands for gas chromatography using a flame ionization detector.

The experimental results are given in Table 1.

TABLE 1

|  | Example |  |  |  |
|---|---|---|---|---|
|  | 1.A | 1.B | 1.C | 1.D |
| Conditions step 1 |  |  |  |  |
| Temperature (° C.) | 60-100 | 100 | 100 | 90 |
| Pressure (bara) | 1 | 2.6 | 10 | 20 |
| Time (hour) | 2 | 0.5 | 0.5 | 2 |
| Conditions step 2 |  |  |  |  |
| Temperature (° C.) | 190 | 190 | 200 | 190 |
| Reaction time (hr) | 2 | 2 | 2 | 2 |
| Starting materials (mol ratio) |  |  |  |  |
| EDA | 2 | 2 | 2 | 2 |
| AEEA | 1 | 1 | 1 | 1 |
| $CO_2$ | 1.6 | 1.5 | 1.7 | 2.5 |
| U-loading after step 2 (mol/kg) | 5.6 | 3.1 | 3.6 | 2.7 |
| $CO_2$/—NH—CH2-CH2—NH— | 0.55 | 0.50 | 0.57 | 0.83 |

The U-loading was defined as the amount of moles of urea groups in the resulting amine mixture per kilogram of reaction mixture. In each of the experiments the molar ratio of EDA:AEEA in the starting mixture was 2:1. In the first step of the process the CO2 was dosed at different pressure levels namely 1, 2.6, 10 and 20 bara. The molar ratio of provided CO2 per mole —NH—CH2-CH2—NH— moiety ranges between 0.50 in example 1.B and 0.83 in example 1.C. For all experiments, even though relatively mild conditions were used, and no—metal or any other—catalyst was added, a good U loading was achieved. This shows that using low pressure CO2 can lead to an unexpected good conversion of ethylene and ethanolamines into urea amines.

EXAMPLE 2

Conversion of EDA, AEEA, DETA, and TETA into their Cyclic Urea Adducts Using CO2 at a Pressure of 10 Bar The process according to the invention can be used to convert various amine molecules into their cyclic urea adducts. This is illustrated in the experiments described below.

Four experiments were carried out: one with aminoethylethanolamine (AEEA), one with diethylenetriamine (DETA), one with triethylenetetramine (TETA) and one with ethylenediamine (EDA) as starting material. For each of these experiments the procedure was the same.

The amine molecule was combined with CO2 in a two-step process. In the first step, the CO2 was loaded into the amine mixture at 100° C. for 30 min. In the second step of the process, the loaded mixture was heated to a temperature of 190° C. for two hours in a closed reactor vessel to obtain a mixture of amines and their cyclic urea adducts. The pressure at the end of the second step (at reaction temperature) was below 15 bara for all experiments. After two hours of reaction time, the reaction mixture was cooled down and analyzed using GC-FID, which stands for gas chromatography using a flame ionization detector.

The experimental results are given in Table 2.

TABLE 2

|  | Example |  |  |  |
|---|---|---|---|---|
|  | 2A | 2B | 2C | 2D |
| Conditions step 1 |  |  |  |  |
| Temperature (Celsius) | 100 | 100 | 100 | 60 |
| Pressure (bar) | 10 | 10 | 10 | 5 |
| Reaction time (min) | 30 | 30 | 30 | 30 |
| Conditions step 2 |  |  |  |  |
| Temperature | 190 | 190 | 190 | 190 |
| Reaction time (min) | 120 | 120 | 120 | 120 |
| Starting materials (mol ratio) |  |  |  |  |
| EDA |  |  |  | 1.0 |
| AEEA | 1.0 |  |  |  |
| DETA |  | 1.0 |  |  |
| TETA |  |  | 1.0 |  |
| CO2 | 0.3 | 0.8 | 0.9 | 0.5 |
| U-loading after step 2 (mol/kg) | 2.1 | 5.5 | 3.7 | 2.9 |
| CO2 per —NH—CH—CH—NH— | 0.33 | 0.83 | 0.43 | 0.51 |

The U-loading was defined as the amount of moles of urea groups in the resulting amine mixture per kilogram of reaction mixture. For all amine molecules a substantial U-loading was attained after step 2 indicating that this procedure is indeed applicable to different amine types (i.e. both ethylene amines as well as ethanol amines). The molar ratio of absorbed CO2 per mole —NH—CH2-CH2—NH— moiety ranges between 0.33 in example 2A and 0.83 in example 2B.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process for manufacturing a cyclic urea adduct of an ethyleneamine compound, the ethyleneamine compound having a linear —NH—CH2-CH2-NH— group, the process comprising the steps of:

in an absorption step, contacting a liquid medium comprising an ethyleneamine compound having a linear —NH—$CH_2$—$CH_2$—NH— group with a $CO_2$-containing gas stream at a pressure of from about 1 to about 20 bara, resulting in the formation of a liquid medium into which $CO_2$ has been absorbed, bringing the liquid medium to cyclic urea formation conditions, and in an urea formation step, forming cyclic urea adduct of the ethyleneamine compound, urea formation conditions including a temperature of at least about 120° C., wherein the total pressure at the end of the urea formation step is at most about 20 bara, and wherein the temperature in the absorption step is lower than the temperature in the urea formation step.

2. The process according to claim 1, wherein the $CO_2$-containing gas stream comprises at least about 95 vol. % of $CO_2$.

3. The process according to claim 1, wherein the $CO_2$-containing gas stream comprises from about 0.01 to about 70 vol. % of $CO_2$.

4. The process of claim 1 wherein the step of contacting the liquid medium with the $CO_2$-containing gas steam in the absorption step is carried out at a temperature from about 0° ° C. to about 200° C.

5. The process of claim 1 wherein the maximum total pressure in the absorption step is from about 1 to about 15 bara.

6. The process of claim 1 wherein temperature in the urea formation step is from about 140° C. to about 400° C.

7. The process of claim 1 wherein the urea formation step is carried out in a closed vessel.

8. The process of claim 1 wherein urea formation step is carried out in a vessel wherein the volume of the liquid medium in the vessel makes up at least 50% of the total volume of the vessel (including head space).

9. The process of claim 1 wherein the pressure at the end of the cyclic urea formation step is below 15 bara.

10. The process of claim 1 wherein the ethyleneamine compound has a linear —NH—$CH_2$—$CH_2$—NH— group, the process comprising the steps of:

in an absorption step contacting a liquid medium comprising an ethyleneamine compound having a linear —NH—$CH_2$—$CH_2$—NH— group with a $CO_2$-containing gas stream at a pressure of from about 1 to about 10 bara, at a temperature of from about 20 to about 110° ° C., wherein the $CO_2$-containing gas stream is added in a continuous manner or in a fed-batch manner, resulting in the formation of a liquid medium into which $CO_2$ has been absorbed, bringing the liquid medium to cyclic urea formation conditions at a temperature of from about 170 to about 220° C. and a pressure of from about 1 to about 10 bara, in a closed vessel, resulting in the formation of cyclic ethylene ureas.

11. The process of claim 1 wherein the ethyleneamine compound is selected from the group of ethyleneamines comprising at least one linear —NH—$CH_2$—$CH_2$—NH— moiety, wherein the compounds may comprise piperazine rings or tertiary amine groups.

12. The process of claim 1 wherein the ethyleneamine compound is selected from the group of linear hydroxyethylethyleneamine compounds having at least one —NH—$CH_2$—$CH_2$—NH— moiety.

13. The process of claim 1 wherein the liquid medium comprises ethylenediamine (EDA) or monoethanolamine (MEA) and an ethyleneamine compound having a linear —NH—$CH_2$—$CH_2$—NH— group.

14. A process for preparing ethyleneamines or urea derivatives thereof, which process comprises the steps of:

manufacturing a cyclic urea adduct of an ethyleneamine compound, the ethyleneamine compound having a linear —NH—$CH_2$—$CH_2$—NH— group, in an absorption step contacting a liquid medium comprising an ethyleneamine compound having a linear —NH—$CH_2$—$CH_2$—NH— group with a $CO_2$-containing gas stream at a pressure of from about 1 to about 20 bara, resulting in the formation of a liquid medium into which $CO_2$ has been absorbed, bringing the liquid medium to cyclic urea formation conditions, and in an urea formation step forming cyclic urea adduct of the ethyleneamine compound, urea formation conditions including a temperature of at least about 110° C., wherein the total pressure at the end of the urea formation step is at most about 20 bara, wherein the temperature in the absorption step is lower than that of the cyclic urea formation step, and where the cyclic urea adduct of an ethyleneamine compound is a cyclic urea adduct of ethyleneamine, reacting the cyclic urea adduct of an ethyleneamine with an ethanolamine-functional compound, or a urea- or carbamate additive thereof, or where the cyclic urea adduct of an ethyleneamine compound is a cyclic urea adduct of a hydroxyethylethyleneamine, reacting the cyclic urea adduct of a hydroxyethylethyleneamine with a ethyleneamine compound, or a urea- or carbamate additive thereof.

15. The process according to claim 14, comprising the steps of:

in an absorption step contacting a liquid medium comprising an ethyleneamine having a linear —NH—$CH_2$—$CH_2$—NH— group and an ethanolamine with a $CO_2$-containing gas stream at a pressure of from about 1 to about 20 bara, resulting in the formation of a liquid medium into which $CO_2$ has been absorbed, bringing the liquid medium to cyclic urea formation conditions, and in an urea formation step forming cyclic urea adduct of the ethyleneamine and cyclic urea adduct or carbamate adduct of ethanolamine, with urea formation conditions including a temperature of at least about 110° C., wherein the total pressure at the end of the urea formation step is at most about 20 bara, wherein the temperature in the absorption step is lower than that in the urea formation step, and reacting the cyclic urea adduct of the ethyleneamine with the ethanolamine or the urea or carbamate derivative thereof.

16. The process according to claim 1, wherein the $CO_2$-containing gas stream comprises from about 4 to about 60 vol. % of $CO_2$.

17. The process according to claim 1, wherein the step of contacting the liquid medium with the $CO_2$-containing gas steam in the absorption step is carried out at a temperature from about 40° C. to about 110° C.

18. The process according to claim 1, wherein the maximum total pressure in the absorption step is from about 1 to about 3 bara.

19. The process according to claim 1, wherein temperature in the urea formation step is from about 170° ° C. to about 220° C.

20. The process according to claim 1, wherein the ethyleneamine compound is selected from ethylenediamine (EDA), diethylenetriamine (DETA), triethylenetetramine (L-TETA), and tetraetylenepentamine (L-TEPA).

\* \* \* \* \*